United States Patent [19]

Kaschig et al.

[11] 4,424,359
[45] Jan. 3, 1984

[54] VINYL-SUBSTITUTED 2,2'-BIPYRIDINE COMPOUNDS

[75] Inventors: Jürgen Kaschig, Freiburg, Fed. Rep. of Germany; Dieter Lohmann, Münchenstein, Switzerland

[73] Assignee: Ciba-Geigy Corporation, Ardsley, N.Y.

[21] Appl. No.: 287,859

[22] Filed: Jul. 27, 1981

[30] Foreign Application Priority Data

Jul. 17, 1980 [CH] Switzerland ............................ 5482/80

[51] Int. Cl.³ .............................................. C07D 401/04
[52] U.S. Cl. ...................................... 546/255; 546/22; 546/24; 546/261; 546/267; 546/266; 546/2; 526/241; 526/265
[58] Field of Search .................... 546/22, 24, 261, 266, 546/267, 255

[56] References Cited

U.S. PATENT DOCUMENTS 3,810,888  5/1974  Chapuriat et al. ............. 260/240 D

OTHER PUBLICATIONS

P. K. Ghosh et al., J. Am. Chem. Soc., vol. 102 pp. 5543–5549 (apparently published Aug. 13, 1980).

Primary Examiner—Robert T. Bond
Attorney, Agent, or Firm—Michael W. Glynn

[57] ABSTRACT

Vinyl-substituted 2,2'-bipyridine compounds of the formula

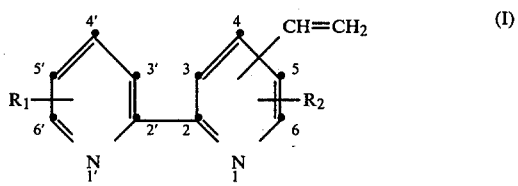

and complexes thereof with metals or metal compounds other than alkali metals or alkaline earth metals, or alkali metal compounds, or alkaline earth metal compounds are described, $R_1$ and $R_2$ being as defined in patent claim 1 and the vinyl group being bonded in the 4-position or 6-position. The 2,2'-bipyridine compounds (I) are suitable for the preparation of complex-forming or complexed, crosslinked or uncrosslinked polymers. Complexed polymers, obtainable from these, are used, for example, as catalysts, in particular for transvinylation reactions. Uncomplexed polymers, which can be prepared from compounds (I), are suitable as metal ion scavengers in various applications.

6 Claims, No Drawings

VINYL-SUBSTITUTED 2,2'-BIPYRIDINE COMPOUNDS

The invention relates to novel vinyl-substituted 2,2'-bipyridine compounds, to novel polymers which can be prepared from these, and to processes for their preparation.

In U.S. Pat. No. 3,810,888 and in German Offenlegungsschriften Nos. 2,037,412 and 2,049,057, complex-forming polymers are described which can carry bipyridine radicals in a side chain or in the main chain. The general definition comprises both polymerisation products and polycondensation products. The concrete disclosure is, however, restricted to the preparation of polycondensation products. The said polymers are suitable for bonding metal ions in various applications. The polymers which can be prepared from these can be employed as catalysts, for example for hydrogenation reactions, dehydrogenation reactions or isomerisation reactions, or for coating metals. It is also known that transition metal complexes, such as metal complexes of poly(styryl)-bipyridines, for example complexes with Pd(O), palladium acetate, or tungsten tetracarbonyl, polystyrene tris-(bipyridyl)-ruthenium-II complexes and bis-(bipyridine)-poly-4-vinylpyridine-ruthenium-II complexes, are suitable as catalysts for various reactions, especially as hydrogenation catalysts or isomerisation catalysts or for photochemical reactions [compare, for example, Inorganic Chemistry, 17, No. 9, 2345 (1978); J. Org. Chem. 44, 1095 (1979) and 43, 2958 (1978); J. Am. Chem. Soc. 100:21, 6635 (1978), Inorganica Chimica Acta, 33, L 139 (1979) and Inorg. Chim. Acta, 44, L 289 (1980)]. Finally, it is disclosed in Polymer Preprints, Japan, 29, 2, 280 (1980) that polymers of 6-vinyl-2,2'-bipyridine can form complexes with transition metals.

The invention relates to novel 2,2'-bipyridine compounds of the formula I

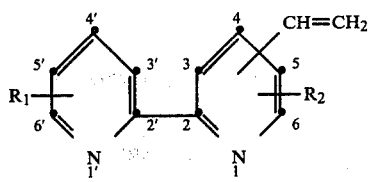

and to complexes thereof with metals or metal compounds other than alkali metals or alkaline earth metals, or alkali metal compounds or alkaline earth metal compounds, wherein the vinyl group is bonded in the 4-position or 6-position, $R_1$ is hydrogen, $C_{1-6}$-alkyl, $C_{1-6}$-alkoxy, phenyl or phenoxy and $R_2$ is hydrogen or methyl, with the proviso that one of $R_1$ and $R_2$ is not hydrogen, if the vinyl group is bonded in the 6-position.

The alkyl and alkoxy groups $R_1$ can be straight-chain or branched, but they are preferably straight-chain and have 1-4 C atoms. Examples of suitable alkyl and alkoxy groups are: the methyl, ethyl, n-propyl, isopropyl, n-butyl, sec.-butyl and tert.-butyl, n-pentyl, 2-pentyl, n-hexyl, methoxy, ethoxy, n-propoxy, isopropoxy, n-butoxy, n-pentyloxy and n-hexyloxy groups.

If the vinyl group is bonded in the 6-position, $R_1$ is preferably hydrogen and $R_2$ is methyl bonded in the 3-position. However, those compounds of the formula I and complexes thereof are preferred in which the vinyl group is bonded in the 4-position, especially those in which $R_1$ is hydrogen or $C_{1-4}$-alkyl bonded in the 4'-position, 5'-position or 6'-position and $R_2$ is hydrogen or methyl. Those compounds of the formula I and complexes thereof are particularly preferred in which the vinyl group is bonded to the 4-position, $R_1$ is methyl bonded in the 4'-position or 6'-position and $R_2$ is hydrogen, or $R_1$ is hydrogen and $R_2$ is methyl bonded in the 6-position. 6-Methyl-4-vinyl-2,2'-bipyridine and its complexes according to the definition are very particularly preferred.

The metals used for forming complexes with compounds of the formula I are, for example, those of main groups IIIa and IVa and of the sub-groups IVb, Vb, VIb, VIIb, VIII, Ib and IIb of the periodic table. Metal compounds which are suitable for the preparation of complexes according to the definition, or in complexes according to the definition, are especially neutral or ionic metal compounds of the abovementioned main groups and sub-groups of the periodic table, for example salts or acids, and in the case of salts the metal can be present either in the anion or in the cation. If desired, the metal atom of the complex, or that of the metal compounds used for the preparation thereof, can additionally also have further coordinative, covalent or ionic bonds which link it to other ions, atoms or molecules, for example to one or more further compounds of the formula I or to a 2,2'-bipyridine radical.

The salts can be salts with either inorganic or organic acids, such as halides, in particular chlorides, nitrates, sulfates, phosphates, perchlorates and carboxylates, such as formates, acetates, propionates and stearates; and also salts which contain a complex anion or cation, for example oxo derivatives of titanium, vanadium, zirconium, molybdenum, hafnium, niobium, tantalum, tungsten and uranium; and anionic metal complexes of halide, cyanide, thiocyanate, thiosulfate and orthophosphate ions, such as tetrachloroplatinate, tetrachloropalladate or hexathiocyanatochromate. Examples of salts or complexes of this type are: stannyl chloride, lead acetate; copper-I or copper-II chloride, bromide or iodide, copper-II acetate, nitrate or sulfate, copper-I cyanide, tetraacetonitrilo-copper-I perchlorate, silver nitrate; zinc chloride, cyanide and thiocyanate, cadmium chloride, cyanide and thiocyanate, mercury iodide or cyanide; zirconium tetrachloride; vanadium-III chloride, vanadium oxysulfate, ammonium metavanadate, niobium-V chloride, tantalum-V chloride, uranium tetrachloride or tetrabromide, uranyl nitrate and acetate; chromium carbonyl, chromium-III chloride, hexathiocyanatochromate, molybdenum oxytrichloride, molybdenum carbonyl, tungsten oxytrichloride, tungsten carbonyl; manganese-II chloride and iodide; iron-III nitrate, phosphate, sulfate or acetate, iron-II or iron-III chloride, ruthenium-III chloride, potassium pentachlorohydroxyruthenate-IV, dichloro-bis-(2,2'-bipyridine)-ruthenium-II, cobalt-II chloride, cobalt-II acetate, nitrate or sulfate, rhodium-II acetate, rhodium-III chloride, potassium rhodium chloride, nickel-II acetate, nickel-II bromide or chloride, nickel-II sulfate, palladium-II chloride or iodide, palladium-IV chloride, palladium acetate, palladium nitrate, potassium tetrachloropalladate, potassium tetrachloroplatinate and potassium hexachloroplatinate.

Complexes with metals and metal compounds of sub-groups Ib, IIb, IVb, Vb, VIb, VIIb and VIII and especially metals and metal compounds of sub-groups Ib and VIII are preferred. Compounds of the formula I, which contain iron, ruthenium, cobalt, nickel, palladium, platinum or copper, especially ruthenium, palladium, platinum or copper, as the complexed central atom are particularly preferred. Complexes with palladium are very particularly preferred.

The acids can be, for example, acids which correspond to the abovementioned salts with a complex anion, such as $H_2PtCl_6$ or $H_2PdCl_4$.

If metal complexes are used for the preparation of 2,2'-bipyridine complexes according to the invention, those metal complexes are preferred which have at least two readily replaceable ligands which are capable of ligand exchange. The valency of the metal complexed with the compound of the formula I is determined by the nature of the metal compounds used for the preparation of the complex or by an oxidation or reduction reaction during or after the formation of the complex.

The compounds of the formula I can be prepared, for example, by oxidising a compound of the formula II

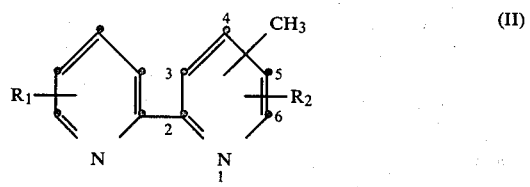

to a compound of the formula IIIa or IIIb

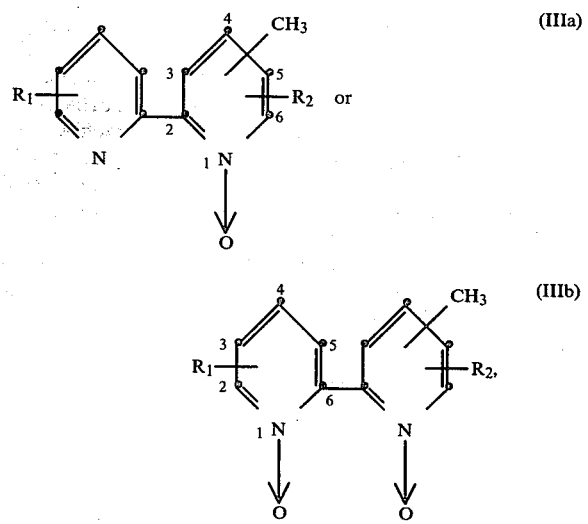

reacting the compound of the formula IIIa and IIIb with a compound of the formula IV

(R'CO)$_2$O  (IV)

to give a compound of the formula Va or Vb

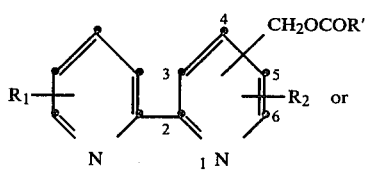

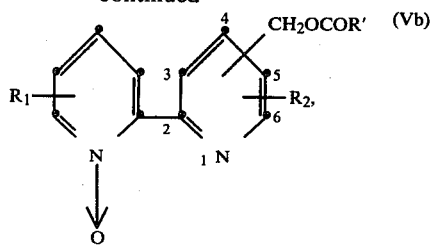

converting the compound of the formula Vb into a compound of the formula Va, saponifying the compound of the formula Va in the presence of a base to give a compound of the formula VI

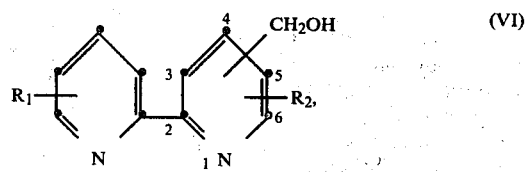

converting the compound of the formula VI by treatment with HCl or HBr into the corresponding chloromethyl or bromomethyl compound of the formula VII

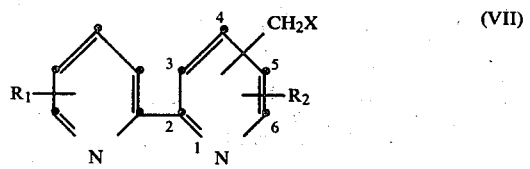

reacting the compound of the formula VII with a compound of the formula VIII

P(R")$_3$  (VIII)

to give a phosphonium salt of the formula IX

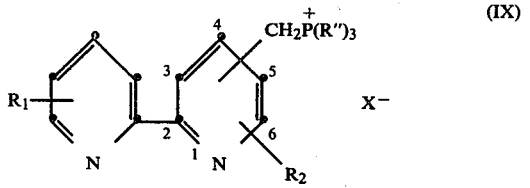

and reacting the phosphonium salt of the formula IX, in the presence of a base, with formaldehyde to give a compound of the formula I. In these formulae, $R_1$ and $R_2$ are as defined under the formula I, X is chlorine or bromine, R' is $C_{1-5}$-alkyl and preferably methyl, and the R" independently of one another are $C_{1-5}$-alkyl or phenyl which is unsubstituted or monosubstituted or disubstituted by $C_{1-4}$-alkyl or $C_{1-4}$-alkoxy, and preferably they are each unsubstituted phenyl. The groups $-CH_3$, $-CH_2OCOR'$, $-CH_2OH$, $-CH_2X$ and $-CH_2P^+(R")_3$ are bonded in the 4-position or 6-position.

Preferably, triphenylphosphine is used as the compound of the formula VIII. If desired, the compounds of the formula I can subsequently be converted in a manner known per se into complexes according to the definition.

Any desired oxidising agents which do not exert any detrimental influence on the remaining constituents of the molecule can in principle be used for the oxidation of the compounds of the formula II to compounds of the formula IIIa or IIIb. Examples of suitable oxidising agents for the above reaction are peracids and organic peroxides and hydroperoxides. Peracids, such as peracetic acid, perpropionic acid, perbenzoic acid, chloroperbenzoic acid or monoperphthalic acids, or peroxides, such as acetaldehyde monoperacetate and dibenzoyl peroxide, are particularly preferred. Advantageously, the oxidation is carried out in the presence of an inert solvent. Examples of suitable solvents are ethyl acetate, water, acetic acid, methylene chloride, acetone and chloroform. The reaction of the compounds of the formula IIIa and IIIb with the anhydrides of the formula IV, preferably acetic anhydride, can be carried out in excess reagent (anhydride of the formula IV) as the solvent or, preferably, in the presence of chlorinated aliphatic hydrocarbons, such as chloroform, dichloromethane or dichloroethane. N-Oxide groups which may still be present are reduced before the further reaction to give compounds of the formula VI, for example by treating compounds of the formula Vb with phosphorus trihalides, triphenyl phosphite or triphenylphosphine. The saponification of the compounds of the formula Va in the presence of a base to give compounds of the formula VI is advantageously carried out in an aqueous-organic medium, preferably in an aqueous-alcoholic medium. The bases used are advantageously alkali metal hydroxides or alkaline earth metal hydroxides, preferably NaOH or KOH. The treatment of the hydroxymethyl compounds of the formula VI with HCl or HBr is expediently carried out at the reflux temperature and with the use of concentrated aqueous hydrochloric or hydrobromic acid. In general, the compounds of the formula VII are directly used further, without an intermediate isolation.

The reaction of the compounds of the formula VII with the phosphines of the formula VIII is advantageously carried out in the presence of an inert organic solvent, such as toluene, tetrahydrofuran or N,N-dimethylformamide, and at temperatures between about 50° to 150° C. The reaction of the phosphonium salts with formaldehyde to give compounds of the formula I is carried out in the presence of a base and, if appropriate, in the presence of a solvent, and in the presence of a phase transfer catalyst and a polymerisation inhibitor. Examples of suitable bases are sodium hydride, n-butyllithium, alkali metal and alkaline earth alcoholates, alkali metal and alkaline earth metal hydroxides, alkali metal and alkaline earth metal carbonates and trialkylamines having 2-4 C atoms in each of the alkyl groups. Preferably, an inert solvent, such as benzene, toluene, tetrahydrofuran, dixoane, N,N-dimethylformamide, methylene chloride, methanol, ethanol or water is used in the reaction. Preferred solvents are water and in particular mixtures of water and a water-insoluble organic solvent, such as methylene chloride. The bases used are preferably alkali metal hydroxides and carbonates. Examples of suitable phase transfer catalysts are crown ethers, cryptants and tetraalkylammonium salts, such as tetra-n-butylammonium bisulfate and tetra-n-butylammonium cyanide. Examples of polymerisation inhibitors are dinitrochloroanilines, phenothiazine derivatives, diarylamines, sulfur, picric acid, α-nitroso-β-naphthol, hydroquinone and phenols, such as di-tert.-butyl-p-cresol.

Compounds of the formula Ia

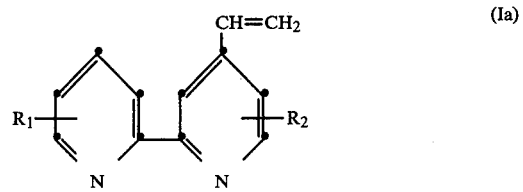

can, according to a new process, also be prepared by either (a) treating a compound of the formula IIa

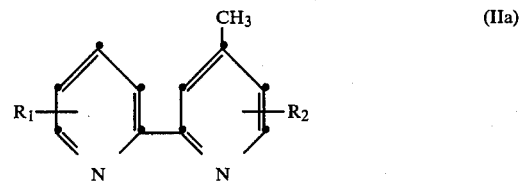

first with a metalating reagent and then converting it with formaldehyde into a compound of the formula X

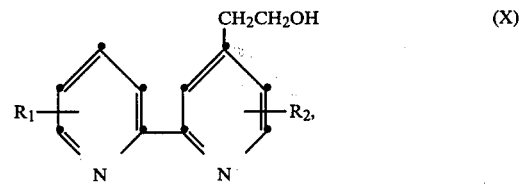

or (b) first treating a compound of the formula IIa with a metalating reagent and then reacting it with a compound of the formula XI HalCH$_2$OCH$_2$R  (XI)

to give a compound of the formula XII

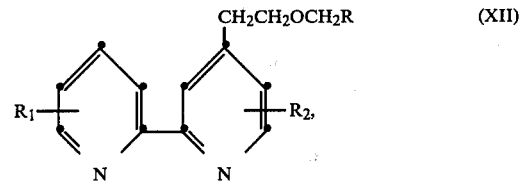

hydrogenating the compound of the formula XII to a compound of the formula X and dehydrating the compound of the formula X to a compound of the formula Ia. In the above formulae, R$_1$ and R$_2$ are as defined under the formula I, Hal is a halogen atom, in particular bromine or chlorine, and R is phenyl which is unsubstituted or substituted by C$_{1-6}$-alkyl or C$_{1-6}$-alkoxy, preferably unsubstituted phenyl. Compounds of the formula Ia can also be obtained by treating compounds of the formula IIa, as described under (b), with a metalating reagent and with compunds of the formula XI and subsequently heating the reaction mixture, without isolating the compounds of the formula XII (thermal elimination). If desired, the compounds of the formula Ia can subsequently be converted into complexes according to the definition, in a manner known per se.

Suitable metalating reagents for the above reactions are especially lithium compounds, for example alkyllithium compounds, such as n-butyllithium or sec.-butyllithium and also benzyllithium, phenyllithium, thienyllithium or lithium alkylamides, such as lithium diisopropylamide. Advantageously, lithium diisopropylamide is used in the presence of hexametylphosphoric acid triamide. Expediently, the reaction is carried out at $-70°$ C. to $+80°$ C., preferably at $0°$ to $25°$ C., in the presence of inert solvents, such as diethyl ether or tetrahydrofuran. The preferred solvent is tetrahydrofuran. Surprisingly, the stated preferred reaction conditions make possible a very selective reaction of compounds of the formula IIa on the $CH_3$ group in the 4-position, without other alkyl groups on the pyridine ring or the azomethine grouping of the pyridine rings being attacked. The further reaction with formaldehyde or with compounds of the formula XI to give compounds of the formula X or XII respectively is advantageously carried out in the same solvent, without isolation of the metalated intermediates obtained.

Mixtures of isomers, as obtained during their preparation, can also be used as the bipyridine compounds of the formula IIa, for example mixtures of 4,6-dimethyl-2,2'-bipyridine, 3,6-dimethyl-2,2'-bipyridine and 3,5-dimethyl-2,2'-bipyridine, but only compounds having a methyl group in the 4-position are converted in this case. If mixtures of isomers are used for the above reactions, process variant (b) is preferred. The compounds of the formula XII thus obtained can readily be purified by distillation to remove unconverted starting products.

The hydrogenation of the compounds of the formula XII to compounds of the formula X is preferably carried out in the presence of an inert organic solvent. Examples of suitable solvents are ethanol, methanol or dioxane, and especially acid media, such as ethanol/hydrogen chloride mixtures, acetic acid or trifluoroacetic acid. Trifluoroacetic acid or its mixture with acetic acid is preferred. The said hydrogenation is advantageously carried out catalytically. Examples of suitable catalysts are copper/chromium oxide and nickel catalysts, such as Raney nickel, and especially noble metal catalysts, such as platinum catalysts and palladium catalysts, and very particularly palladium-on-carbon catalysts.

The dehydration of the compounds of the formula X is expediently carried out in the presence of an alkali metal hydroxide, such as sodium hydroxide or potassium hydroxide. Advantageously, this is effected without a solvent at temperatures between about $130°$ and $200°$ C. In the direct conversion of reaction mixtures containing compounds of the formula XII into compounds of the formula Ia, temperatures of $120°-200°$ C. and pressures of 133 to 0.1 Pa are advantageously used.

The conversion of the compounds of the formula I or Ia into the complexes according to the definition, if this is desired, is carried out in a manner known per se, for example by contacting the compounds of the formula I in an undissolved or dissolved form with a solution or suspension of a suitable metal compound. Examples of suitable reaction media are water, N,N-dimethylformamide, N,N-dimethylacetamide, acetonitrile, dioxane and tetrahydrofuran. The metal compounds used can be, for example, metal salts or acids of the type mentioned above, especially halides or carboxylates, or metal complexes having at least two replaceable coordinated ligands which can undergo a ligand exchange, such as tetraacetonitrilo-copper-I perchlorate, dichlorobis-(2,2'-bipyridine)ruthenium-II and potassium tetrachloroplatinate.

The compounds of the formulae II, IIa, IV, VIII and XI are known or can be prepared by methods known per se. Compounds of the formula II or IIa can, for example, be obtained by reacting substituted or unsubstituted cyanopyridines with suitable alkynes in the presence of cobalt catalysts [compare, for example, Synthesis, 600 (1975)].

The starting materials or intermediates of the formulae IIIa, IIIb, Va, Vb, VI, VII, IX, X and XII, which were specifically developed for the preparation of the compounds of the formula I, according to the invention, are still novel and likewise form a subject of the invention. The preferred definitions given above for R, R', R", $R_1$ and $R_2$ here also apply.

The compounds of the formula I and their complexes according to the definition represent valuable starting materials for the preparation of complex-forming or complexed polymers.

The invention therefore relates also to novel crosslinked or uncrosslinked polymers which are obtainable by polymerising 2 to 100 mol % of a compound of the formula I and/or of a complex of a compound of the formula I with metals or metal compounds other than alkali metals or alkaline earth metals, or alkali metal compounds or alkaline earth metal compounds, and 0 to 98 mol % of a compound of the formula A)

in which $X_1$ is hydrogen, $X_2$ is hydrogen, chlorine or methyl and $X_3$ is hydrogen, methyl, chlorine, —CN, —COOH, —CONH$_2$, phenyl, methylphenyl, methoxyphenyl, cyclohexyl, pyridyl, imidazolyl, pyrrolidyl, —COO-alkyl having 1–12 C atoms in the alkyl, —COO-phenyl,

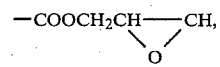

—COO-alkyl—OH having 1–4 C atoms in the alkyl, —OCO-alkyl having 1–4 C atoms in the alkyl, —OCO-phenyl, —CO-alkyl having 1–3 C atoms in the alkyl, alkoxy having 1–20 C atoms or phenoxy, or $X_2$ is hydrogen and $X_1$ and $X_3$ conjointly are an anhydride grouping, a —CO—NR'"—CO—grouping or are each —COOH or —COOalkyl having 1–16 C atoms in the alkyl, R'" being straight-chain or branched $C_{1-18}$-alkyl, cyclohexyl or phenyl which can be monosubstituted or disubstituted by $C_{1-6}$-alkyl, halogen, cyano, nitro and/or $C_{1-3}$-alkoxy, in the presence of 0 to 60 mol % of a polyunsaturated crosslinking agent and, if desired, converting complex-forming polymers thus obtained into polymers which are wholly or partially complexed with metal or metal compounds other than alkali metals or alkaline earth metals, or alkali metal compounds or alkaline earth metal compounds.

If complexes of compounds of the formula I are used, in which the metal atom, such as copper, iron or ruthenium, is coordinated with further compounds of the formula I, crosslinked polymers are formed even without the use of additional crosslinking agents.

Those compounds of the formula (A) are preferred in which $X_1$ is hydrogen, $X_2$ is hydrogen or methyl and $X_3$ is —$CONH_2$, phenyl, pyridyl, pyrrolidyl, —COO-alkyl-OH having 2–4 C atoms in the alkyl or —COO-alkyl having 1–12 C atoms in the alkyl part. Styrene, methyl acrylate, 2-ethylhexyl acrylate and 2-hydroxyethyl methacrylate are very particular preferred.

Examples of suitable polyunsaturated crosslinking agents are divinylbenzenes, divinylpyridines, divinyltoluenes, divinylnaphthalenes, divinylxylenes, divinylethylbenzenes, divinylsulfone, divinyl ketone, divinyl sulfide, divinyl sebacate, trivinylbenzenes, trivinylnaphthalenes and polyvinylanthracene; ethylene glycol diacrylate, ethylene glycol dimethacrylate, allyl acrylate, diallyl phthalate, diallyl maleate, diallyl fumarate, diallyl succinate, diallyl carbonate, diallyl malonate, diallyl oxalate, diallyl adipate, diallyl sebacate, diallyl tartrate, diallyl silicate, triallyl tricarballylate, triallyl aconitate, triallyl citrate, triallyl phosphate, N,N'-methylenediacrylamide, N,N'-methylenedimethylacrylamide, N,N'-ethylenediacrylamide, and polyallyl ethers and polyvinyl ethers of ethylene glycol, propanetriol, pentaerythritol, resorcinol and the monothio or dithio derivatives of ethylene glycol. The crosslinking agent is preferably employed in a quantity of 1 to 30 mol %. Preferred crosslinking agents are divinylpyridine and in particular divinylbenzene. The degree of swelling of the polymers can be adapted to the desired specific applications by a suitable selection of the comonomers and/or crosslinking agents.

Those linear polymers are preferred which have a mean molecular weight from 1,000 to 5,000,000 and which consist of 3 to 100 mol % of recurrent structural units having the formula (B)

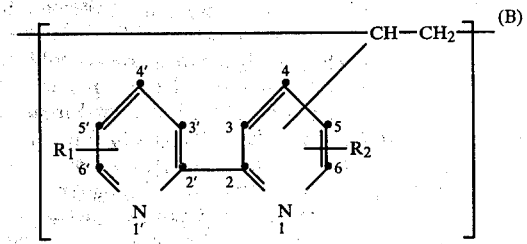

and/or complexes of such structural units with metals or metal compounds other than alkali metals or alkaline earth metals, or alkali metal compounds or alkaline earth metal compounds, the metal atoms not being coordinated with further structural units having the formula (B) and the groups —CH—$CH_2$— being bonded in the 4-position or 6-position, and of 0 to 97 mol % of recurrent structural units having the formula (C)

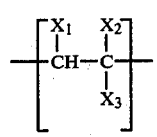

in which $R_1$ and $R_2$ are as defined under the formula I and $X_1$, $X_2$ and $X_3$ are as defined under the formula (A), and in particular those polymers of this type which have a mean molecular weight from 2,000 to 3,000,000, and/or complexes thereof, and which consist of 3 to 100 mol % of recurrent structural units having the formula (B), and/or complexes, according to the definition, of such structural units having the formula (B), and of 0 to 97 mol % of recurrent structural units having the formula (C), in which the group —CH—$CH_2$— is bonded in the 4-position, $R_1$ is methyl bonded in the 4'-position or 6'-position and $R_2$ is hydrogen, or $R_1$ is hydrogen and $R_2$ is methyl bonded in the 6-position, $X_1$ is hydrogen, $X_2$ is hydrogen or methyl and $X_3$ is —$CONH_2$, phenyl, pyridyl, pyrrolidyl, —COO-alkyl-OH having 2–4 C atoms in the alkyl or —COO-alkyl having 1–12 C atoms in the alkyl, and 5 to 100 percent of the structural units having the formula (B) being complexed with metals or metal compounds other than alkali metal or alkaline earth metals, or alkali metal compounds or alkaline earth metal compounds. Particularly preferably, $X_1$ is hydrogen, $X_2$ is hydrogen or methyl and $X_3$ is phenyl, —$COOCH_2CH_2OH$, —$COOCH_3$ or

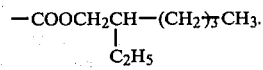

Preferred complexing metals or metal compounds in crosslinked or linear polymers according to the invention are those of the type mentioned under the formula I. Crosslinked or linear polymers which contain a metal of sub-groups Ib or VIII, in particular iron, ruthenium, cobalt, nickel, palladium, platinum or copper, especially ruthenium, palladium, platinum or copper and very particularly palladium as the complexed central atoms, are very particularly preferred.

The above linear polymers can be obtained by polymerising 3 to 100 mol % of a compound of the formula I and/or of a complex of a compound of the formula I with metals or metal compounds other than alkali metals or alkaline earth metals, or alkali metal compounds or alkaline earth metal compounds, the metal atom not being coordinated with further compounds of the formula I, with 0 to 97 mol % of a compound of the formula (A) and, if desired, subsequently converting complex-forming polymers thus obtained into polymers which are wholly or partially complexed with metals or metal compounds other than alkali metals or alkaline earth metals or alkali metal compounds or alkaline earth metal compounds, the metal atoms not being coordinated with further compounds of the formula I.

Moreover, those crosslinked polymers are preferred which are obtained by reacting linear polymers having a mean molecular weight from 1,000 to 5,000,000 and consisting of 3 to 100 mol % of recurrent structural units having the formula (B) and 0 to 97 mol % of recurrent structural units having the formula (C), with 5 to 100 mol % of tetraacetonitrilo-copper-I perchlorate. The linear polymers used here are advantageously those of the preferred type indicated above.

The conversion, if desired, of the polymers obtained according to the invention into wholly or partially complexed polymers can be carried out analogously to the procedure described above for the bipyridine compounds of the formula I.

The polymerisation of compounds of the formula I or complexes thereof with metal or metal compounds other than alkali metals or alkaline earth metals, or alkali metal compounds or alkaline earth metal compounds, and their copolymerisation with compounds of the formula (A), if appropriate in the presence of polyunsaturated cross-linking agents, can be carried out in a manner known per se, for example in the presence of conventional anionic initiators. Free-radical polymerisation is preferred. In this case, about 0.01 to 5% by weight, preferably 0.01 to 1.5% by weight, relative to the total weight of the monomers and crosslinking agents, of free-radical initiators known per se, such as inorganic or organic peroxides or azo compounds, for example hydrogen peroxide, potassium peroxydisulfate, tert.-butyl hydroperoxide, di-tert.-butyl peroxide, peracetic acid, dibenzoyl peroxide, diacyl peroxides, cumene hydroperoxide, tert.-butyl perbenzoate, tert.-alkyl peroxydicarbonates and $\alpha,\alpha'$-azoisobutyronitrile, are advantageously used. The reaction temperatures for the free-radical polymerisation are in general between about 30° and 100° C. The free-radical polymerisation can, however, also be carried out in th cold, for which purpose redox systems can also be used in the above-mentioned concentrations, for example mixtures of peroxides, such as hydrogen peroxide, and a reducing agent, such as divalent iron ions. The polymerisation can be carried out in a homogeneous phase, for example in bulk or in solution, or in a heterogeneous phase, that is to say as a precipitation polymerisation, emulsion polymerisation or suspension polymerisation. Polymerisation in solution is preferred. Examples of suitable solvents are toluene, N,N-dimethylformamide, N,N-dimethylacetamide and acetonitrile.

The wholly or partially complexed polymers, which can be prepared according to the invention, can be employed as catalysts, for example as hydrogenation catalysts for example for the hydrogenation of alkenes or alkynes, as isomerisation catalysts or as catalysts for the acetoxylation of benzene. Complexes, according to the definition, of compounds of the formula I can also be used as catalysts. Especially because of their insolubility in the customary reaction media, however, polymers which are complexed in accordance with the invention are preferred for this application.

Polymers according to the invention, which are at least partially complexed with palladium or a palladium compound, in particular palladium acetate, are suitable, with good efficiency, especially as catalysts for transvinylation reactions. Their activity is comparable to that of homogeneous catalysts, such as are generally used for transvinylation reactions. Compared with previously known transvinylation catalysts, such as potassium tetrachloropalladate, they have the advantage of being directly re-usable for further reactions, without reprocessing.

Uncomplexed polymers according to the invention can be used for the preparation of corresponding complexed polymers. Such complex-forming polymers—and also the compounds of the formula I—are, however, also used as metal ion scavengers, for example for the extraction of noble metals, rare earths and radioactive elements, such as uranium, from their ores or minerals, for the separation of radioactive cesium from other metals, or for the separation of different metals (with the exception of alkali metals and alkaline earth metals), for the recovery of chromium salts from tannery effluents, for the demineralisation of organic solvents without introducing extraneous ions, for the preparation of dielectric fluids, and for the purification of industrial effluents in order to remove undesired metal ions.

After the binding of the metal ions, the complexes obtained can be reconverted into the complex-forming polymers or complex-forming compounds of the formula I, for example by elution with strong acids or with complex-forming agents, such as ethylenediamine or ethylenediaminetetraacetic acid.

Using the compounds of the formula I and their complexes, linear polymers having virtually any desired mean molecular weight can be prepared. By using suitable comonomers and/or crosslinking agents, so-called tailor-made polymers can be prepared, that is to say polymers of which the composition and the number of complex-forming or complexed bipyridine units is adapted to the specific applications. The crosslinked or uncrosslinked polymers which can be prepared using the compounds of the formula I and complexes thereof are additionally distinguished by a high stability to thermal or chemical degradation.

The examples which follow serve to illustrate the invention.

EXAMPLE 1

4-Vinyl-6-methyl-2,2'-bipyridine (a) Preparation of 4-[2-(benzyloxy)-ethyl]-6-methyl-2,2'-bipyridine 36.4 g (0.2 mol) of a mixture of isomers, consisting of 4,6-dimethyl-2,2'-bipyridine (45% by weight), 3,6-dimethyl-2,2'-bipyridine (45% by weight) and 3,5-dimethyl-2,2'-bipyridine (10% by weight) are dissolved in 150 ml of anhydrous tetrahydrofuran (THF). At 0° C., a solution of lithium diisopropylamide and hexamethylphosphoric acid triamide in THF/n-hexane [ratio about 1:1 by volume; prepared from 12.2 g (0.12 mol) of diisopropylamine in 50 ml of anhydrous THF, 60 ml of 2-molar n-butyllithium solution in n-hexane and 25.9 g (0.12 mol) of anhydrous hexamethylphosphoric acid triamide] is added dropwise in the course of 2 hours. Subsequently, the mixture is stirred for 30 minutes at 0° C. and for 15 minutes at 23° C. At −75° C., 20.3 g (0.13 mol) of benzyl chloromethyl ether are added dropwise in the course of 30 minutes. The reaction mixture is warmed slowly to 23° C., stirred for 1 hour at this temperature and then added to 200 ml of 10% hydrochloric acid. The solution is washed with three times 250 ml of ethyl acetate. The aqueous phase is rendered alkaline with potassium carbonate and the product obtained is extracted with four times 250 ml of ethyl acetate. The combined ethyl acetate phases are dried over sodium sulfate and the solvent is removed in vacuo. The residue is distilled in a high vacuum. The initial fraction (16.8 g; boiling point 75°–83° C./0.27 Pa) contains 78% by weight of 3,6-dimethyl-2,2'-bipyridine, 14% by weight of 3,5-dimethyl-2,2'-bipyridine and 3% by weight of unconverted 4,6-dimethyl-2,2'-bipyridine. At 174°–176° C./0.09 Pa, 20.3 g of 4-[2-(benzyloxy)-ethyl]-6-methyl-2,2'-bipyridine distil over; yield 78% of theory, calculated on the 4,6-dimethyl-2,2'-bipyridine present in the mixture of isomers employed. $n_D^{20} = 1.6007$.

Analysis for $C_{20}H_{20}N_2O$: calculated C 78.92%, H 6.63%, N 9.20%, found C 78.70%, H 6.69%, N 9.40%.

(b) Preparation of 4-(2-hydroxyethyl)-6-methyl-2,2'-bipyridine

Method A: 4.4 g of palladium-on-carbon (5% by weight of Pd) are added to a solution of 22 g (0.072 mol) of 4-[2-(benzyloxy)-ethyl]-6-methyl-2,2'-bipyridine in 110 ml of trifluoroacetic acid, and the hydrogenation is carried out at 25° C. After 30 minutes, the absorption of hydrogen (1.78 l) ceases. After filtering off the catalyst, the mixture is freed from solvent in vacuo and the oily residue is dissolved in 2 N hydrochloric acid. The solution is washed with ethyl acetate and then rendered alkaline with potassium carbonate (pH 9). The 4-(2-hydroxyethyl)-6-methyl-2,2'-bipyridine is extracted with four times 150 ml of ethyl acetate. After washing the combined organic phases with saturated sodium chloride solution and after drying over sodium sulfate, the solvent is distilled off in vacuo. After standing for several hours, the residue crystallises, and it can be recrystallised from n-hexane/ethyl acetate. Yield 13.5 g (87% of theory); melting point 56° C.

Analysis for $C_{13}H_{14}N_2O$: calculated C 72.88%, H 6.59%, N 13.08%, O 7.47%, found C 72.60%, H 6.80%, N 13.05%, O 7.46%.

Method B: 16.6 g (0.0876 mol) of a mixture of isomers of dimethyl-2,2'-bipyridines [composition as indicated above under (a)] are dissolved in 50 ml of anhydrous THF. At 0° C., a solution of lithium diisopropylamide and hexamethylphosphoric acid triamide in THF/n-hexane [ratio about 1:1 by volume; prepared from 10.1 g (0.1 mol) of diisopropylamine in 50 ml of anhydrous THF, 50 ml of 2-molar n-butyllithium solution in n-hexane and 18 g (0.1 mol) of anhydrous hexamethylphosphoric acid triamide] is added dropwise. Subsequently, the mixture is stirred for 30 minutes at 0° C. and for 30 minutes at 40° C. At 0° to 10° C., formaldehyde gas [prepared by pyrolysis of paraformaldehyde] is passed in, until the colour changes from black to yellow. After heating to 40° C. for 5 minutes, 250 ml of dilute hydrochloric acid are added, while cooling with ice. After washing with three times 300 ml of ethyl acetate, the mixture is rendered alkaline with potassium carbonate, and the reaction product is extracted with three times 350 ml of ethyl acetate. The extract is washed with saturated ammonium sulfate solution, dried over sodium sulfate and freed from solvent in vacuo. The residue is heated in a high vacuum (4 Pa) to a maximum of 130° C. during which the mixture of 3,6-dimethyl-2,2'-bipyridine (73% by weight), 3,5-dimethyl-2,2'-bipyridine (3% by weight) and unconverted 4,6-dimethyl-2,2'-bipyridine (8% by weight) distils off, in addition to hexamethylphosphoric acid triamide. After chromatography of the residue (8.9 g) over silica gel (eluent toluene/acetone, ratio 1:1 by volume) and recrystallisation from n-hexane/ethyl acetate, 4.2 g of 4-(2-hydroxyethyl)-6-methyl-2,2'-bipyridine are obtained in a crystalline form (50% of theory), calculated on the 4,6-dimethyl-2,2'-bipyridine present in the mixture of isomers employed.

(c) Preparation of 4-vinyl-6-methyl-2,2'-bipyridine

Method A: 7.6 g of powdered potassium hydroxide, 5.4 g of aluminium oxide beads ("Spheralite SCS" ® 9 3/6 mm from Messrs. Rhône-Poulenc Ind.) and 0.2 g of hydroquinone are heated in a retort to 170° C. Under a pressure of 6.7 Pa, 10.9 g (0.051 mol) of molten 4-(2-hydroxyethyl)-6-methyl-2,2'-bipyridine are added dropwise. The reaction product distils off continuously at 100°–105° C. After redistillation, 8.7 g (87% of theory) of 4-vinyl-6-methyl-2,2'-bipyridine are obtained. Boiling point 90°–91° C./0.40 Pa. UV absorption (in chloroform): $\lambda_{max}=288$ nm ($\epsilon=10,200$).

Analysis for $C_{13}H_{12}N_2$: calculated C 79.56%, H 6.16%, N 14.27%, found C 79,36%, H 6.19%, N 14.38%.

Method B: 500 g (2.75 mols) of a mixture of isomers, consisting of 4,6-dimethyl-2,2'-bipyridine (45% by weight), 3,6-dimethyl-2,2'-bipyridine (45% by weight) and 3,5-dimethyl-2,2'-bipyridine (10% by weight), are reacted in accordance with the procedure of Example 1(a). The crude product formed is heated under 133 to 400 Pa for 2 hours at 120° to 125° C. and then for 45 minutes at 170° C. (bath temperature). 299 g of a distillate are thus obtained which has a boiling range of 65°–107° C. and which is composed of 65% by weight of 3,6-dimethyl-2,2'-bipyridine, 7% by weight of 3,5-dimethyl-2,2'-bipyridine as well as 17% by weight of benzyl alcohol and 10% by weight of hexamethylphosphoric acid triamide. The residue is heated under 0.1 Pa and, in a boiling range of 48°–170° C., a mixture distils off which is subjected to a fractional redistillation after di-tert.-butyl-p-cresol has been added as a polymerisation inhibitor. Thus, 51 g of (4-(2-benxyloxy)-ethyl)-6-methyl-2,2'-bipyridine, 11 g of 3,6- and 3,5-dimethyl-2,2'-bipyridine, 105 g of benzyl alcohol and 147 g of 4-vinyl-6-methyl-2,2'-bipyridine (61% of theory) are obtained.

EXAMPLE 2

3-Methyl-6-vinyl-2,2'-bipyridine (a) Preparation of 3,6-dimethyl-2,2'-bipyridine 1,1'-dioxide 19 g (0.103 mol) of 3,6-dimethyl-2,2'-bipyridine are stirred for 66 hours at 23° C. with 17.3 g (0.227 mol) of anhydrous peracetic acid (as a 2.28-molar solution in ethyl acetate). After adding about 200 ml of ethylbenzene, the mixture is concentrated in vacuo, ethylbenzene is again added and the mixture is concentrated once more. The crystalline residue is recrystallised from chlorobenzene. 18.9 g (85% of theory) of 3,6-dimethyl-2,2'-bipyridine 1,1'-dioxide are obtained; melting point 225°–230° C.

Analysis for $C_{12}H_{12}N_2O_2$: calculated C 66.66%, H 5.60%, N 12.96%, O 14.80%, found C 66.1% H 5.6%, N 12.6%, O 15.1%.

(b) Preparation of 3-methyl-6-acetoxymethyl-2,2'-bipyridine 1'-oxide

A solution of 4 g (0.018 mol) of 3,6-dimethyl-2,2'-bipyridine 1,1'-dioxide in 20 ml chloroform is added dropwise, at 60° C. and under a nitrogen atmosphere, to 20 ml of acetic anhydride. The mixture is stirred for 20 hours at 60°–65° C. and then concentrated in vacuo. After the addition of 50 ml of water and 50 ml of ethyl acetate, the mixture is rendered alkaline with potassium carbonate. The water phase is separated off and washed with four times 50 ml of ethyl acetate/THF (ratio about 2:1 by volume). The combined organic phases are dried over sodium sulfate. After the solvent has been distilled off in vacuo, 4.44 g (96% of theory) of a brown crude product are obtained, which can be caused to crystallise at 0° C. The crude product can be employed direct for further reactions. After recrystallisation from diethyl ether, 73% of pure 3-methyl-6-acetoxymethyl-2,2'-bipyridine 1'-oxide are obtained; melting point 105°–107° C.

Analysis for $C_{14}H_{14}O_3N_2$: calculated: C 65.11%, H 5.46%, N 10.85%, O 18.58%, found: C 65.23%, H 5.48%, N 10.87%, O 18.43%.

(c) Preparation of 3-methyl-6-acetoxymethyl-2,2'-bipyridine 2.1 g (8.1 mmols) of 3-methyl-6-acetoxymethyl-2,2'-bipyridine 1'-oxide are dissolved in 20 ml of benzene at 45° C., and 1.43 g (10.4 mmols) of phosphorus trichloride are added dropwise under an atmosphere of nitrogen. Subsequently, the mixture is boiled under reflux for 30 minutes. After cooling to 23° C., 35 ml of water are added and the benzene phase is separated off. The water phase is washed with twice 15 ml of ethyl acetate. The combined organic phases are dried over sodium sulfate and concentrated in vacuo. After distillation in a bulb tube oven at 125° C./0.13 Pa, 1.51 g (77% of theory) of 3-methyl-6-acetoxymethyl-2,2'-bipyridine are obtained in the form of a colourless oil.

Analysis for $C_{14}H_{14}N_2O_2$: calculated: C 69.41%, H 5.83%, N 11.57%, O 13.21%, found: C 68.93%, H 5.58%, N 11.54%, O 13.12%.

(d) Preparation of 3-methyl-6-hydroxymethyl-2,2'-bipyridine 1.4 g (5.8 mmols) of 3-methyl-6-acetoxymethyl-2,2'-bipyridine are boiled under reflux for 30 minutes in a mixture of 20 ml of 10% sodium hydroxide solution and 15 ml of ethanol. After cooling, the mixture is acidified with hydrochloric acid and washed with twice 20 ml of ethyl acetate. The aqueous phase is rendered alkaline with potassium carbonate, and the reaction product is extracted with 40 ml of ethyl acetate. After drying over sodium sulfate and concentration in vacuo, the 3-methyl-6-hydroxymethyl-2,2'-bipyridine is crystallised from diethyl ether. Yield: 0.99 g (85% of theory); melting point 51°–53° C. UV absorption (in chloroform): $\lambda_{max}=281$ nm ($\epsilon=9400$).

Analysis for $C_{12}H_{12}N_2O$: calculated: C 71.98%, H 6.04%, N 13.99%, O 7.99%, found: C 71.68%, H 5.97%, N 13.86%, O 8.00%.

(e) Preparation of 3-methyl-6-bromomethyl-2,2'-bipyridine 0.9 g (4.5 mmols) of 3-methyl-6-hydroxymethyl-2,2'-bipyridine are boiled under reflux for 6 hours, together with 5 ml of 62% hydrobromic acid. After cooling, 10 ml of water and 20 ml of diethyl ether are added. The water phase is rendered alkaline with potassium carbonate, separated from the ether phase and washed with a further 10 ml of diethyl ether. The combined ether phases are dried over sodium sulfate and concentrated to dryness in vacuo (maximum bath temperature: 30° C.). 1.16 g (98% of theory) of 3-methyl-6-bromomethyl-2,2'-bipyridine remains as an oily product which decomposes at room temperature, giving a red colouration, and crystallises at 0° C. The 3-methyl-6-bromomethyl-2,2'-bipyridine is immediately used further.

(f) Preparation of [3-methyl-2,2'-bipyridin-6-yl-(methylene)]-triphenylphosphonium bromide 1.16 g (4.4 mmols) of 3-methyl-6-bromomethyl-2,2'-bipyridine together with 1.39 g (5.3 mmols) of triphenylphosphine in 50 ml of N,N-dimethylformamide are heated at 80° C. for 3 hours. At 23° C. and with rapid stirring, 50 ml of diethyl ether are added. The precipitating oily product crystallises after a short time and is filtered off with suction. After recrystallisation from 25 ml of water, 1.14 g (49% of theory) of [3-methyl-2,2'-bipyridin-6-yl-(methylene)]-triphenylphosphonium bromide are obtained in the form of colourless crystals; melting point 214°–215° C.

Analysis for $C_{30}H_{26}BrN_2P.1H_2O$: calculated C 66.30%, H 5.19%, N 5.16%, Br 14.70%, P 5.70%, found C 66.61%, H 5.26%, N 5.23%, Br 14.98%, P 5.72%.

(g) Preparation of 3-methyl-6-vinyl-2,2'-bipyridine 0.9 g (1.7 mmols) of [3-methyl-2,2'-bipyridin-6-yl-(methylene)]-triphenylphosphonium bromide monohydrate is dissolved in a well stirred emulsion consisting of 15 ml of 35% formaldehyde solution, 20 ml of dichloromethane, 5 mg of di-tert.-butyl-p-cresol and 22 mg of tetrabutylammonium cyanide. A solution of 0.5 g of sodium hydroxide in 2.5 ml of water is added dropwise at 25° C. After stirring for 1 hour at 23° C., the dichloromethane phase is separated off and washed with 20 ml of water. After the addition of 5 mg of di-tert.-butyl-p-cresol, the mixture is concentrated in vacuo and 20 ml of dilute hydrochloric acid are added to the residue. The precipitating crystalline triphenylphosphine oxide is washed with three times 20 ml of ethyl acetate. The aqueous phase is covered with a layer of 20 ml of ethyl acetate and rendered alkaline with potassium carbonate. The organic phase is dried over sodium sulfate and freed from solvent in vacuo. After renewed addition of 5 mg of di-tert.-butyl-p-cresol, the residue is distilled in a bulb tube oven at a maximum of 150° C./0.93 Pa. 0.24 g (71% of theory) of 3-methyl-6-vinyl-2,2'-bipyridine are obtained as a colourless liquid. UV absorption (in chloroform): $\lambda=250$ nm ($\epsilon=15,450$); $\lambda=293$ nm ($\epsilon=7,700$).

Analysis for $C_{13}H_{12}N_2$: calculated: C 79.56%, H 6.16%, N 14.27%, found: C 79.05%, H 6.27%, N 13.92%.

EXAMPLE 3

4-Methyl-4'-vinyl-2,2'-bipyridine

(a) Preparation of 4,4'-dimethyl-2,2'-bipyridine 1-oxide 27.6 g (0.15 mol) of 4,4'-dimethyl-2,2'-bipyridine are dissolved in 300 ml of dichloromethane. 86 ml of a 1.837-molar solution of peracetic acid in ethyl acetate are added dropwise at 23°–28° C. After stirring for 50 hours at 23° C., the mixture is concentrated in vacuo. 27.2 g (90% of theory) of 4.4'-dimethyl-2,2'-bipyridine 1-oxide crystallise from ethylbenzene/petroleum ether; melting point 80°–130° C. (over a range).

Analysis for $C_{12}H_{12}N_2O$: calculated: C 71.98%, H 6.04%, N 13.99%, O 7.99%, found: C 71.70%, H 6.23%, N 13.97%, O 8.16%.

(b) Preparation of 4-methyl-4'-acetoxymethyl-2,2'-bipyridine 25.5 g (0.127 mol) of 4,4'-dimethyl-2,2'-bipyridine 1-oxide in 130 ml of chloroform are added to 260 ml of acetic anhydride. After stirring for 20 hours at 60°–65° C., chloroform and acetic anhydride are largely distilled off in vacuo. 250 ml of water and 250 ml of ethyl acetate/THF (ratio 2:1 by volume) are added to the residue, and the mixture is rendered alkaline with potassium carbonate. The water phase is washed with 150 ml of ethyl acetate/THF (ratio 2:1 by volume). The combined organic phases are dried over sodium sulfate. After removal of the solvent in vacuo, a black oil mixed with crystals is obtained. The major quantity of the crystalline fraction is separated off by washing with diethyl ether and sublimation at about 100° C./0.093 Pa. After two distillations at 122°–123° C./0.093 Pa, 14.3 g of an inhomogeneous product are obtained, which is used directly for the further reaction. IR (NaCl): 1770 (vs), 1620 (s) and 1230 (vs) cm$^{-1}$.

(c) Preparation of 4-methyl-4'-hydroxymethyl-2,2'-bipyridine

A mixture of 9.4 g of the crude product obtained according to Example 3(b), 130 ml of 10% sodium hydroxide solution and 50 ml of ethanol is boiled under reflux for 30 minutes. Subsequently, the ethanol is distilled off and the residue is acidified with hydrochloric acid. After it has been washed with 200 ml of ethyl acetate, the water phase is rendered alkaline with potassium carbonate, and the reaction product is extracted with twice 80 ml of ethyl acetate. After drying over sodium sulfate and treatment with active charcoal, the mixture is concentrated in vacuo. By means of an addition of petroleum ether, 3.1 g of crystals are obtained which are recrystallised from diethyl ether. Yield of 4-methyl-4'-hydroxymethyl-2,2'-bipyridine: 1.6 g (5.3% of theory), relative to the 4,4'-dimethyl-2,2'-bipyridine 1-oxide starting product; melting point 110°–112° C.

Analysis for $C_{12}H_{12}N_2O$: calculated: C 71.98%, H 6.04%, N 13.99%, O 7.99%, found: C 72.10%, H 6.10%, N 13.85%, O 8.03%.

The yield, determined by NMR spectroscopy after working-up of the mother liquor, amounts to about 30 to 40% of theory, relative to 4,4'-dimethyl-2,2'-bipyridine 1-oxide. The by-product formed (4,4'-dimethyl-3-hydroxy-2,2'-bipyridine) can be separated off by double sublimation at 70°–90° C./0.67 Pa and subsequent recrystallisation from cyclohexane: melting 88°–90° C.

$^1$H-NMR (CDCl$_3$) $\delta$=2.33 (s; 3H); 2.43 (s, 3H); 7.08 (m; 2H); 8.06 (m; 1H); 8.31 (m, 1H); 8.42 (m; 1H); 9.57 (s; 1H) ppm.

(d) Preparation of 4-methyl-4'-bromomethyl-2,2'-bipyridine 1.5 g of 4-methyl-4'-hydroxymethyl-2,2'-bipyridine are reacted analogously to Example 2(e). This gives 1.74 g (88% of theory) of 4-methyl-4'-bromomethyl-2,2'-bipyridine as an unstable oil which is used immediately for the further reaction.

(e) Preparation of [4-methyl-2,2'-bipyridin-4'-yl-(methylene)]-triphenylphosphonium bromide 1.74 g (6.6 mmols) of 4-methyl-4'-bromomethyl-2,2'-bipyridine are reacted analogously to Example 2(f). After recrystallisation from water, 2.7 g (77% of theory) of [4-methyl-2,2'-bipyridin-4'-yl-(methylene)]-triphenylphosphonium bromide are obtained; melting point 260°–265° C.

Analysis for $C_{30}H_{26}BrN_2P.0.38\ H_2O$: calculated: C 67.70%, H 5.07%, N 5.26%, Br 15.01%, P 5.82%, found: C 67.78%, H 5.29%, N 5.27%, Br 14.91%, P 5.94%.

(f) Preparation of 4-methyl-4'-vinyl-2,2'-bipyridine 1.4 g (2.7 mmols) of [4-methyl-2,2'-bipyridin4'-yl-(methylene)]-triphenylphosphonium bromide are reacted analogously to Example 2(g). 0.36 g (70% of theory) of 4-methyl-4'-vinyl-2,2'-bipyridine are obtained in the form of colourless crystals; melting point 82°–86° C. UV absorption (in chloroform): $\lambda_{max}$=281 nm ($\epsilon$=10,600).

Analysis for $C_{13}H_{12}N_2$: calculated C 79.56%, H 6.16%, N 14.27%, found: C 79.45%, H 6.20%, N 14.15%.

EXAMPLE 4

Bis-(2,2'-bipyridine)-(4-vinyl-6-methyl-2,2'-bipyridine)-ruthenium-II perchlorate

[Ru(bipy)$_2$(4V6Mebipy)](ClO$_4$)$_2$

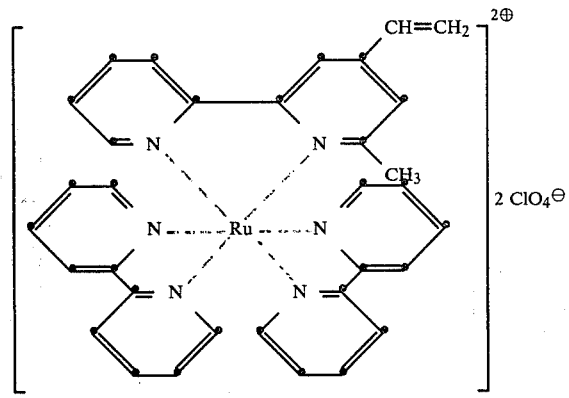

0.176 g (8.97×10$^{-4}$ mol) of 4-vinyl-6-methyl-2,2'-bipyridine is dissolved in 150 ml of degassed ethanol. After the addition of 0.5 g (8.99×10$^{-4}$ mol) of dichloro-bis-(2,2'-bipyridine)-ruthenium-II with about 4 equivalents of water of crystallisation, the mixture is heated to the reflux temperature for 2 hours under a nitrogen atmosphere. The solvent is removed in vacuo and the residue is dissolved in about 100 ml of water. Red crystals are precipitated by adding 10 ml of 1 N perchloric acid. After recrystallisation from hot water and drying at 25° C./0.13 Pa, 0.693 g (94% of theory) of the above product is obtained.

Absorption of UV and visible light (in water): $\lambda$=244 ($\epsilon$=33,650), 287 ($\epsilon$=65,500) and 452 nm ($\epsilon$=13,650).

Analysis for $C_{33}H_{28}N_6Cl_2O_8Ru.(0.68\ H_2O)$: calculated: C 48.29%, H 3.62%, N 10.24%, Cl 8.64%, Ru 12.31%, H$_2$O 1.49%, found: C 48.35%, H 3.49%, N 10.22%, Cl 8.15%, Ru 12.4%, H$_2$O 1.49%.

EXAMPLE 5

Dichloro-(4-vinyl-6-methyl-2,2'-bipyridine)-platinum-II

[Pt(4V6Mebipy)Cl$_2$]

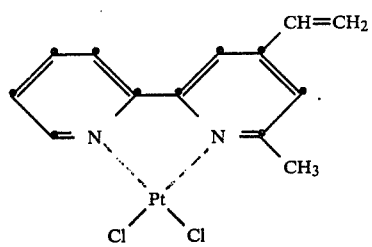

A mixture of 0.830 g (2×10$^{-3}$ mol) of potassium tetrachloroplatinate in 100 ml of water, 0.432 g (2.2×10$^{-3}$ mol) of 4-vinyl-6-methyl-2,2'-bipyridine and 4 ml of 2 N hydrochloric acid is boiled for 30 minutes. After cooling, the yellow crystals which have precipitated are filtered off with suction. After concentration of the filtrate, further product is obtained. The product is recrystallised from N,N-dimethylacetamide/water.

Analysis for $C_{13}H_{12}Cl_2N_2Pt$:

calculated: C 33.78%, H 2.62%, N 6.06%, Cl 15.34%, Pt 42.20%, found: C 34.01%, H 2.82%, N 6.20%, Cl 15.27%, Pt 41.8%.

EXAMPLE 6

Poly-[1-(6-methyl-2,2'-bipyridin-4-yl)-ethylene]

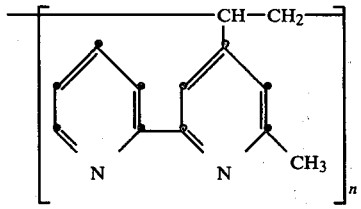

In an ampoule flushed with nitrogen, 10 mg of azobisisobutyronitrile (AIBN) are added to 4 g (0.0204 mol) of freshly distilled 4-vinyl-6-methyl-2,2'-bipyridine. The ampoule is heated for 16 hours at 70° C., with exclusion of air. The glassy product formed is dissolved in chloroform. A white powder is obtained by pouring the solution into about 250 ml of diethyl ether. Yield 3.8 g (95% of theory). Intrinsic viscosity (chloroform): $[\eta] = 1.0$ dl/g. Mean molecular weight $\overline{M}_2 = 530{,}000$.

Glass transition temperature Tg = 141° C. UV absorption (in chloroform): $\lambda = 240$ ($\epsilon = 10{,}600$), 288 nm ($\epsilon = 12{,}100$).

Analysis for $(C_{13}H_{12}N_2)_n$: calculated: C 79.56%, H 6.16%, N 14.27%, found: C 79.28%, H 6.20%, N 14.23%.

EXAMPLE 7

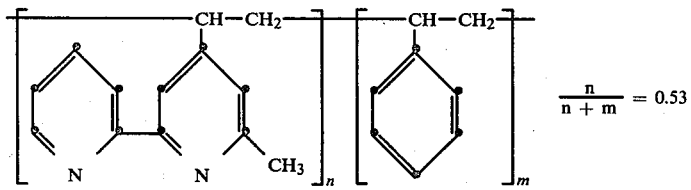

1 g ($5.1 \times 10^{-3}$ mol) of freshly distilled 4-vinyl-6-methyl-2,2'-bipyridine and 0.47 g ($4.5 \times 10^{-3}$ mol) of freshly distilled styrene are mixed, in an ampoule flushed with nitrogen, with 5 mg of AIBN and are polymerised analogously to Example 6. 1.4 g (95% of theory) of a white fibrous product are obtained by precipitation from tetrahydrofuran/n-hexane. Intrinsic viscosity (chloroform): $[\eta] = 2.5$ dl/g. $\overline{M}_w = 1{,}700{,}000$. Glass transition temperature Tg = 138° C. UV absorption (in chloroform): $\lambda = 288$ nm ($\epsilon = 11{,}800$).

Analysis for $(C_{13}H_{12}N_2)_n(C_8H_8)_m$ with $n/(n+m) = 0.53$: calculated: C 83.62%, H 6.67%, N 9.33%, found: C 83.08%, H 6.61%, N 9.95%.

EXAMPLE 8

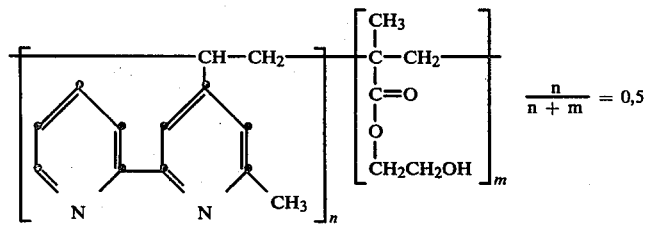

Analogously to Example 7, 1 g of 4-vinyl-6-methyl-2,2'-bipyridine and 0.664 g ($5.9 \times 10^{-3}$ mol) of 2-hydroxyethyl methacrylate are copolymerised. The polymer dissolves incompletely (gel particles) in N,N-dimethylformamide. It is precipitated from water and freeze-dried.

Analysis for $(C_{13}H_{12}N_2)_n(_6H_{10}O_3)_m$ with $n/(n+m) = 0.5$: calculated: C 69.92%, H 6.79%, N 8.58%, found: C 69.48, H 6.56%, N 8.76%.

EXAMPLE 9

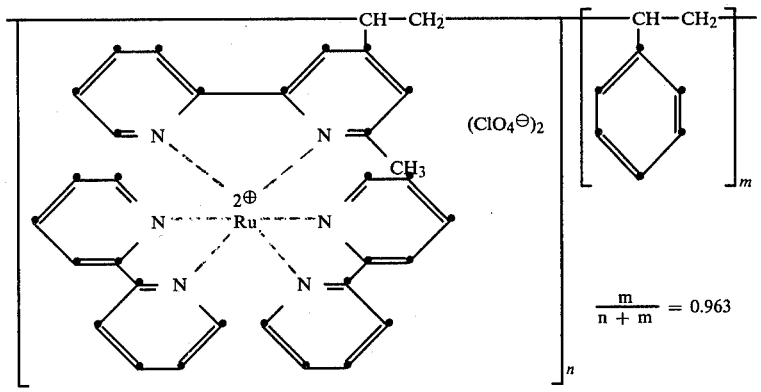

A mixture of 2.86 mg of AIBN and 1 ml of N,N-dimethylacetamide (distilled under argon) is added to 64 mg (7.91×10$^{-5}$ mol) of the bis-(2,2'-bipyridine)-(4-vinyl-6-methyl-2,2'-bipyridine)-ruthenium-II perchlorate prepared according to Example 4, in an ampoule filled with argon. 165 mg of freshly distilled styrene are added to the red solution obtained. The ampoule is heated for 19 hours at 70° C., with exclusion of air. After the solution has been poured into 15 ml of methanol and this mixture has been centrifuged, an orange-coloured product is obtained which is purified by repeated suspending in methanol and subsequent centrifuging. Yield: 46.3 mg (20% of theory). Absorption of UV and visible light (in N,N-dimethylformamide): λ=290, 444 nm.

Analysis for $(C_{33}H_{28}N_6Cl_2O_8Ru)_n(C_8H_8)_m$ with n/(n+m)=0.963: calculated: C 82.25%, H 6.75%, N 2.39%, Cl 2.20%, found: C 82.31%, H 6.76%, N 2.29%, Cl 2.22%.

EXAMPLE 10

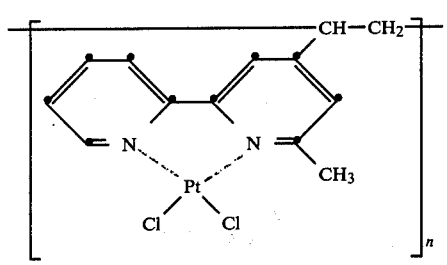

Analogously to Example 6, 300 mg (6.49×10$^{-4}$ mol) of the dichloro-(4-vinyl-6-methyl-2,2'-bipyridine)-platinum-II, prepared according to Example 5, dissolved in 1 ml of N,N-dimethylacetamide are polymerised in the presence of 1.298×10$^{-5}$ mol of AIBN. A green-yellow precipitate deposits from the dark yellow solution. The supernatant liquid phase becomes colourless. The precipitate is washed with water, methanol and diethyl ether. 277 mg (92% of theory) of a yellow insoluble powder are obtained.

Analysis for $(C_{13}H_{12}Cl_2N_2Pt)_n$: calculated: C 33.78%, H 2.62%, N 6.06%, Cl 15.34%, Pt 42.20%, found: C 34.20%, H 2.81%, N 6.21%, Cl 15.32%, Pt 41.98%.

EXAMPLE 11

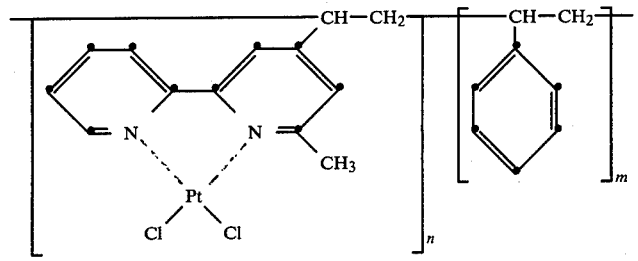

Analogously to Example 9, 98.3 mg (2.127×10$^{-4}$ mol) of the dichloro-(4-vinyl-6-methyl-2,2'-dipyridine)-platinum-II, prepared according to Example 5, dissolved in 2.7 ml of N,N-dimethylacetamide and 443 mg (4.253×10$^{-4}$ mol) of styrene are copolymerised in the presence of 4.466×10$^{-5}$ mol of AIBN. After precipitation from 125 ml of diethyl ether and washing of the precipitate with diethyl ether in methanol, 116.4 mg (22% of theory) of a pale yellow product are obtained. $\eta_{reduced}$ (0.5% in N,N-dimethylacetamide)=0.11 dl/g.

EXAMPLE 12

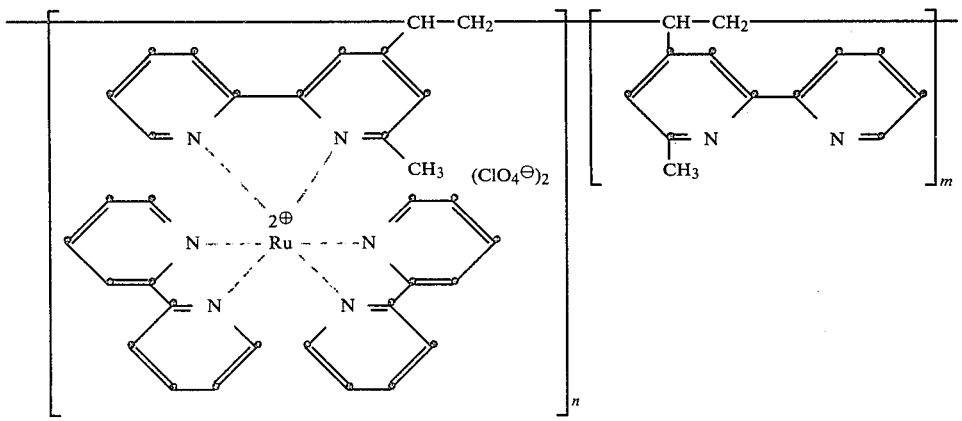

$\dfrac{m}{n+m} = 0.938$ 0.176 g ($8.97\times10^{-4}$ mol of recurring units) of the poly-[1-(6-methyl-2,2'-bipyridin-4-yl)-ethylene] prepared according to Example 6 is dissolved in 150 ml of degassed N,N-dimethylformamide. After the addition of 1 g ($1.80\times10^{-3}$ mol) of dichloro-bis-(2,2'-dipyridine)ruthenium-II with about 4 equivalents of water of crystallisation, the mixture is heated for 15 hours at 140° C. under a nitrogen atmosphere. The solvent is largely removed in vacuo and the residue is poured into a mixture of 10 ml of 1 N perchloric acid and 100 ml of water. The precipitate is centrifuged off and washed several times with water and with methanol. 165 mg of a brick-red powder are obtained. The composition of the copolymer is calculated to be m/(m+n)=0.938 from the absorption of UV and visible light (in N,N-dimethylformamide) at $\lambda=452$ nm ($\epsilon=42$ at $c=2\times10^{-2}$ g/100 ml).

EXAMPLE 13

Reaction product of poly-[1-(6-methyl-2,2'-bipyridin-4-yl)-ethylene] with tetraacetonitrilo-copper-I perchlorate.

A solution of 0.85 g ($4.33\times10^{-3}$ mol of recurring units) of the poly-[1-(6-methyl-2,2'-bipyridin-4-yl)-ethylene], preparing according to Example 6, in 25 ml of N,N-dimethylformamide is added to a solution of 1.5 g ($4.33\times10^{-3}$ mol) of tetracetonitrilo-copper-I perchlorate in 50 ml of N,N-dimethylformamide. The reaction mixture is stirred for 15 hours at 23° C. and the red-brown oil formed is filtered off with suction. The product is washed with 350 ml of N,N-dimethylformamide and then with 500 ml of water as well as ethanol and diethyl ether. After drying at 80° C./13,000 Pa, 1.07 g (89% of theory) of a finely pulverulent product are obtained.

Analysis for $(C_{26}H_{24}N_4ClO_4Cu)_n$: calculated: C 56.22%, H 4.35%, N 10.09%, Cl 6.38%, Cu 11.44%, found: C 51.67%, H 4.35%, N 9.34%, Cl 6.16%, Cu 12.4%.

EXAMPLE 14

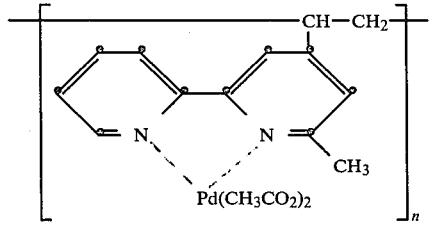

A solution of 0.697 g of palladium-II acetate in 15 ml of tetrahydrofuran is added to a solution of 0.595 g ($3.03\times10^{-3}$ mol) of poly-[1-(6-methyl-2,2'-bipyridin-4-yl)-ethylene] in 90 ml of tetrahydrofuran. The mixture is stirred for 16 hours at 23° C. The yellow-brown precipitate is filtered off with suction and washed with about 250 ml of tetrahydrofuran. Yield 1.08 g (85% of theory).

Analysis for $(C_{17}H_{18}N_2O_4Pd)_n$: calculated: C 48.53%, H 4.31%, N 6.66%, Pd 25.29%, found: C 47.89%, H 4.42%, N 6.65%, Pd 24.4%.

EXAMPLE 15

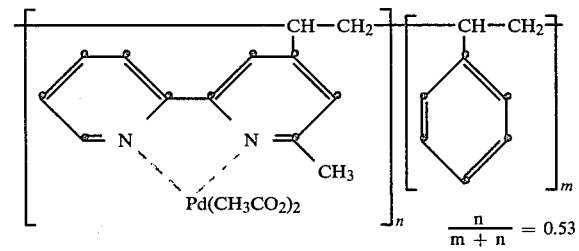

$\dfrac{n}{m+n} = 0.53$ 300.4 mg (1 mmol) of the copolymer prepared according to Example 7 are reacted with 230 mg of palladium-II acetate, analogously to Example 14. Yield 420 mg (80% of theory).

Analysis for $(C_{17}H_{18}N_2O_4Pd)_n(C_8H_8)_m$ with n/n+m=0.53: calculated: C 56.40%, H 4.93%, N 5.46%, Pd 20.74%, found: C 56.36%, H 5.30%, N 5.34%, Pd 19.70%.

EXAMPLE 16

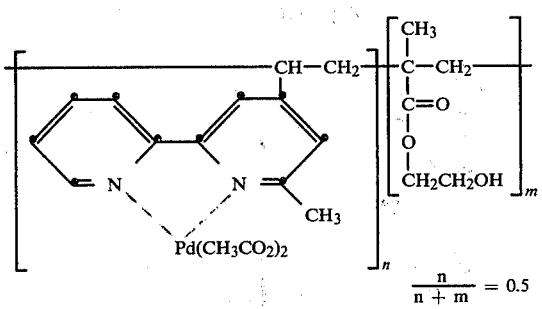

326.4 mg (1 mmol) of the copolymer obtained according to Example 8 are reacted with 230 mg of palladium-II acetate, analogously to Example 14. Yield 436 mg (79% of theory).

Analysis for $(C_{17}H_{18}N_2O_4Pd)_n(C_6H_{10}O_3)_m$ with $n/n+m=0.5$: calculated: C 50.15%, H 5.12%, N 5.09%, Pd 19.31%, found: C 50.24%, H 5.29%, N 5.24% Pd 18.50%.

EXAMPLE 17

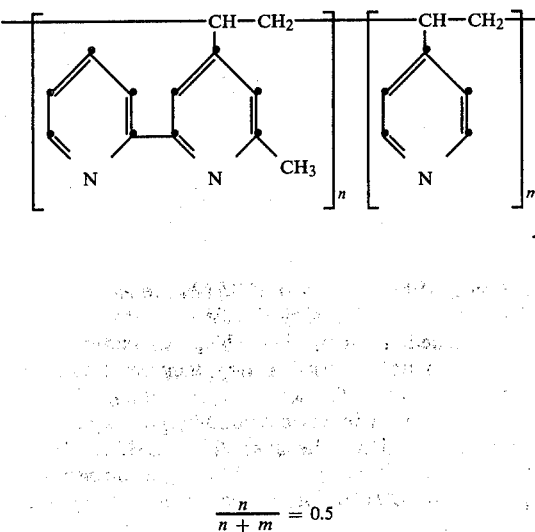

A mixture of 2 g $(1.02 \times 10^{-2}$ mol) of freshly distilled 4-vinyl-6-methyl-2,2'-bipyridine and 1.17 g $(1.02 \times 10^{-2}$ mol) of freshly distilled 4-vinylpyridine is dissolved in 10 ml of N,N-dimethylacetamide. 10 mg $(6.083 \times 10^{-5}$ mol) of AIBN are added to the solution in an ampoule flushed with nitrogen, and the mixture is polymerised analogously to Example 6. A white powder is obtained by pouring the solution into water. The product is dissolved in tetrahydrofuran (THF) and reprecipitated from diethyl ether. Yield 2.27 g; viscosity (chloroform): $\eta_{reduced}=0.52$ dl/g; glass transition temperature: $Tg=155°$ C.

Analysis for $(C_{13}H_{12}N_2)_n(C_7H_7N)_m$ with $n/(n+m)=0.50$: calculated: C 76.63%, H 6.54%, N 13.41%, found: C 76.83%, H 6.21%, N 13.40%.

EXAMPLE 18

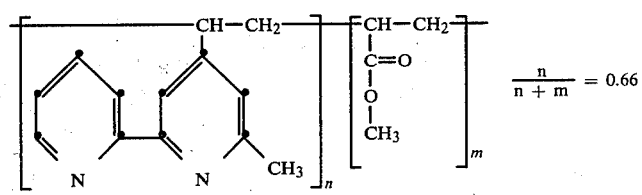

2 g of 4-vinyl-6-methyl-2,2'-bipyridine and 1.13 g $(1.02 \times 10^{-3}$ mol) of N-vinylpyrrolidone are copolymerised analogously to Example 17. The product is precipitated with diethyl ether and dissolved in THF. By pouring the solution into water, a white powder is obtained which is reprecipitated from THF/diethyl ether. Yield 1.87 g; viscosity (chloroform): $\eta_{reduced}=0.44$ dl/g; Glass transition temperature: $Tg=150°$ C.

Analysis for $(C_{13}H_{12}N_2)_n(C_6H_9NO)_m$ with $n/(n+m)=0.75$: calculated: C 77.22%, H 6.48%, N 14.01%, O 2.29%, found: C 77.47%, H 6.33%, N 13.82%, O 2.26%.

EXAMPLE 19

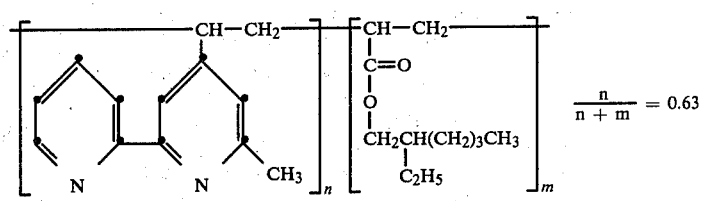

2 g of 4-vinyl-6-methyl-2,2'-bipyridine and 0.87 g $(1.02 \times 10^{-2}$ mol) of methyl acrylate are copolymerised analogously to Example 17. The product is precipitated with water and reprecipitated from THF/cyclohexane. This gives a white powder. Yield: 2.18 g; viscosity (chloroform): $\eta_{reduced}=0.36$ dl/g; glass transition temperature: $Tg=120°$ C.

Analysis for $(C_{13}H_{12}N_2)_n(C_4H_6O_2)_m$ with $n/(n+m)=0.66$: calculated: C 74.86%, H 6.33%, N 11.45%, O 7.36%, found: C 74.22%, H 6.26%, N 11.60%, O 7.73%.

EXAMPLE 20

2 g of 4-vinyl-6-methyl-2,2'-bipyridine and 1.87 g $(1.02 \times 10^{-2}$ mol) of 2-ethylhexyl acrylate are copolymerised analogously to Example 17. By pouring the product at −10° to −15° C. into a mixture of 400 ml of water, 300 ml of isopropanol and 100 ml of methanol, a flocky product is obtained which deliquesces at room temperature to give a highly viscous oil. This is dissolved in THF and reprecipitated from methanol at −25° C. After drying, a coloured powder is obtained. Yield: 2.46 g; viscosity (chloroform): $\eta_{reduced}=0.34$ dl/g; glass transition temperature: Tg=72° C.

Analysis for $(C_{13}H_{12}N_2)_n(C_{11}H_{20}O_2)_m$ with n/(n+m)=0.63: calculated: C 76.77%, H 7.86%, N 9.20%, O 6.17%, found: C 76.80%, H 7.67%, N 9.54%, O 6.37%.

EXAMPLE 21

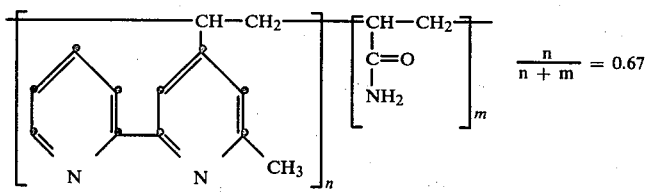

2 g of 4-vinyl-6-methyl-2,2'-bipyridine and 0.72 g ($1.02 \times 10^{-2}$ mol) of acrylamide are copolymerised analogously to Example 17. The product is precipitated from water and dissolved in THF. The solution is filtered and the clear filtrate is stirred into diethyl ether. This gives a white powder. Yield: 1.88 g; viscosity (chloroform): $\eta_{reduced}=0.39$ dl/g; glass transition temperature: Tg=156° C.

Analysis for $(C_{13}H_{12}N_2)_n(C_3H_5NO)_m$ with n/(n+m)=0.67 calculated: C 75.19%, H 6.30%, N 15.10%, O 3.41%, found: C 75.61%, H 6.24%, N 14.57%, O 3.79%.

EXAMPLE 22

Polymer from n mols of 6-methyl-4-vinyl-2,2'-bipyridine, m mols of styrene and o mols of divinylbenzene, with n/(n+m+o)=0.1.

A mixture of 3 g ($1.53 \times 10^{-2}$ mol) of freshly distilled 4-vinyl-6-methyl-2,2'-bipyridine, 14.08 g (0.135 mol) of styrene, 400 mg ($3.06 \times 10^{-3}$ mol, 2 mol %) of technical grade divinylbenzene and 75.6 mg ($4.6 \times 10^{-4}$ mol) of AIBN are added to 40 ml of a 0.1 percent solution of polyvinyl alcohol in water (serum). The suspension is stirred (700 rpm) for 14 hours at 70° C. and for 6 hours at 100° C. The white, finely particulate product is filtered off with suction, washed with water and allowed to swell in 200 ml of THF for 2 hours at the boil. The gel is stirred into 4 liters of water and, after separation, is extracted for 20 hours with THF in a Soxhlet extractor. The gel is dried for 16 hours at 80° C./2,666 Pa and then for 16 hours at 60° C./1.33 Pa. Yield: 15.2 g; swelling factor (THF): Q=2.4.

Analysis for $(C_{13}H_{12}N_2)_n(C_8H_8)_m(C_{10}H_{10})_o$ with n/n+m+o=0.10, o/(n+m+o)=0.02: calculated: C 90.07%, H 7.47%, N 2.46%, found: C 88.68%, H 7.37%, N 2.57%.

EXAMPLE 23

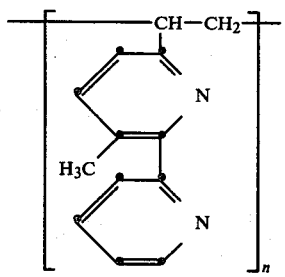

7.54 mg ($4.59 \times 10^{-5}$ mol) of AIBN are added to 3 g ($1.53 \times 10^{-2}$ mol) of freshly distilled 3-methyl-6-vinyl-2,2'-bipyridine in an ampoule flushed with nitrogen, and the mixture is polymerised analogously to Example 6. The glassy product formed is dissolved in 70 ml of THF. A white powder is obtained by pouring the solution into 1,000 ml of n-hexane. Yield: 2.85 g; intrinsic viscosity (chloroform); $[\eta]=1.27$ dl/g; mean molecular weight: $\overline{M}_w=520,000$; glass transition temperature Tg=107° C.

Analysis for $(C_{13}H_{12}N_2)_n$: calculated: C 79.56%, H 6.16%, N 14.27%, found: C 78.12%, H 5.89%, N 14.23%.

EXAMPLE 24

Polymer from n mols of 3-methyl-6-vinyl-2,2'-bipyridine, m mols of styrene and o mols of divinylbenzene with n/(n+m+o)=0.1.

Analogously to Example 22, 1.5 g ($7.64 \times 10^{-3}$ mol) of 3-methyl-6-vinyl-2,2'-bipyridine, 7.04 g. ($6.73 \times 10^{-2}$ mol) of styrene and 200 mg ($1.53 \times 10^{-3}$ mol, 2 mol %) of technical grade divinylbenzene are copolymerised in 20 ml of serum by means of 37.8 mg ($2.3 \times 10^{-4}$ mol) of AIBN, and the mixture is worked up. Yield: 7.2 g; swelling factor (THF); Q=2.5.

Analysis for $(C_{13}H_{12}N_2)_n(C_8H_8)_m(C_{10}H_{10})_o$ with n/(n+m+o)=0.1 and o/(n+m+o)=0.02: calculated: C 90.07%, H 7.47%, N 2.46%, found: C 89.55%, H 7.86%, N 2.51%.

EXAMPLE 25

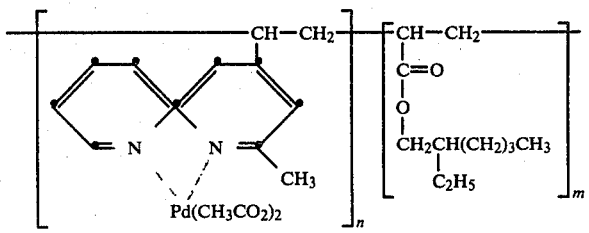

$$\frac{n}{n+m} = 0.63$$

Analogously to Example 14, 500 mg (2.61 mmols of bipyridine units) of the copolymer obtained according to Example 20 are reacted with 644 mg (2.87 mmols) of palladium-II acetate. After extraction with THF and drying, 850 mg of a light brown powder are obtained. The product has a palladium content of 24.7% by weight.

EXAMPLE 26

Polymer from n mols of 6-methyl-4-vinyl-2,2'-bipyridine, m mols of styrene and o mols of divinylbenzene with n/(n+m+o)=0.1, fully complexed with palladium-II acetate.

Analogously to Example 14, 2.7 g of the copolymer obtained according to Example 22 are reacted with 670 mg of palladium-II acetate, the copolymer being suspended as a swollen gel. After extraction with THF and drying, 3.06 g of a brown product having a palladium content of 8.48% by weight are obtained. Swelling factor (THF): Q=2.2.

EXAMPLE 27

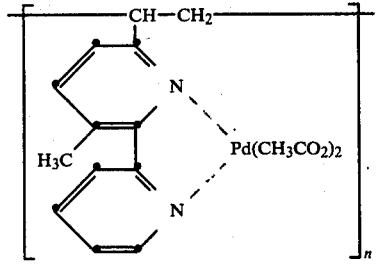

Analogously to Example 14, 200 mg of poly-[1(3-methyl-2,2'-bipyridin-6-yl)-ethylene] are reacted with 275 mg of palladium-II acetate. 430 mg of a light brown powder having a palladium content of 26.2% by weight are obtained.

EXAMPLE 28

Analogously to Example 14, 300 mg of poly-[1-(3-methyl-2,2'-bipyridin-6-yl)-ethylene] are reacted with 34.3 mg of palladium-II acetate. 330 mg of a beige powder having a palladium content of 4.58% by weight are obtained.

EXAMPLE 29

Polymer from n mols of 3-methyl-6-vinyl-2,2'-bipyridine, m mols of styrene and o mols of divinylbenzene with n/(n+m+o)=0.1, fully complexed with palladium-II acetate.

Analogously to Example 26, the copolymer obtained according to Example 24 is reacted with palladium-II acetate. Yield: 3.0 g. Swelling factor (THF): Q=2.1, palladium content: 8.5% by weight.

Application examples: Use as a transvinylation catalyst

EXAMPLE I 0.225 g of the polymer (catalyst) prepared according to Example 14 and having a palladium content of 24.4% by weight are suspended, together with 12.2 g (0.1 mol) of benzoic acid and 0.005 g of 2,6-di-tert.-butyl-p-cresol, in 55.4 ml of vinyl acetate. Under dry nitrogen, the reaction mixture is warmed to 60°–65° C., the course of the reaction being monitored by gas chromatography. After a total of 22 hours, the liquid is decanted from the catalyst, the acetic acid formed and the unconverted benzoic acid are removed by means of extraction by shaking with aqueous sodium bicarbonate solution and the vinyl benzoate is isolated by fractional distillation. Yield of vinyl benzoate=11 g (0.074 mol, corresponding to 74% of theory); boiling point 94°/1,064 Pa. After the catalyst has been separated off, the reaction mixture has a Pd content of less than 2 ppm.

The catalyst which has been decanted off is resuspended in the mixture of benzoic acid, 2,6-di-tert.-butyl-p-cresol and vinyl acetate, and the mixture is warmed under nitrogen to 60°–65° C. After a further 31 hours, 10.6 g=0.072 mol of vinyl benzoate have again formed, corresponding to a yield of 72% of theory.

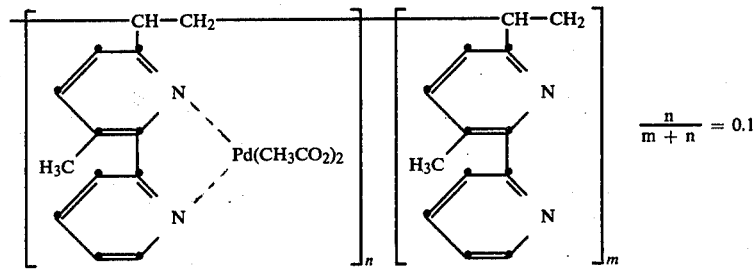

$$\frac{n}{m+n} = 0.1$$

EXAMPLE II

Analogously to the procedure described in Example I, 0.285 g of the polymer prepared according to Example 16 and having a palladium content of 18.5% by weight, are warmed to 60°–65° C. with 12.2 g of benzoic acid and 55.4 ml of vinyl acetate. After 29 hours, 11.3 g of vinyl benzoate have formed, corresponding to a yield of 76% of theory. Using the recovered catalyst, 10.4 g of vinyl benzoate, corresponding to 70.5% of theory are again obtained after 20 hours in a further reaction batch.

EXAMPLE III

Analogously to the procedure described in Example I, 0.28 g of the polymer prepared according to Example 15 and having a palladium content of 19.7% by weight are warmed with 12.2 g of benzoic acid and 55.4 ml of vinyl acetate. In the first reaction run, 76% of theory of vinyl benzoate are isolated after 22 hours. In a further reaction batch with the same polymer, 76% of theory of vinyl benzoate are obtained after 20 hours.

EXAMPLE IV

A mixture of 44.4 ml (0.48 mol) of vinyl acetate and 9.77 g (0.08 mol) of benzoic acid is warmed to 65° C. 500 mg ($4 \times 10^{-4}$ equivalents of Pd) of the polymer (catalyst) obtained according to Example 26 are added. After 1, 2, 3, 5, 7, 12, 17, 24 and 30 hours, 0.6 ml are taken from the reaction mixture each time, and the conversion is determined by gas chromatography (1-chloronaphthalene as the internal standard). The time-/conversion curve shows a maximum yield of vinyl benzoate of 61% after about 15 hours (establishment of the equilibrium). After the catalyst has been separated off, the reaction mixture has a Pd content of less than 2 ppm.

EXAMPLE V

Corresponding to the procedure described in Application Example IV, 500 mg ($4 \times 10^{-4}$ equivalents of Pd) of the polymer obtained according to Example 25 are used as the catalyst. After 30 hours, the measured yield of vinyl benzoate is 58.6%.

EXAMPLES VI–VIII

According to the methods described in Example IV, further polymers according to the invention are used as transvinylation catalysts. The results are indicated in the table which follows.

TABLE

| Application Example No. | Catalyst according to | Quantity of catalyst (mg) | Equivalents of Pd | Yield of vinyl benzoate Yield after 3 hours | Yield of vinyl benzoate Yield after 30 hours |
|---|---|---|---|---|---|
| VI | Example 27 | 168 | $4 \times 10^{-4}$ | 17.4% | 21.7% |
| VII | Example 28 | 168 | $7.2 \times 10^{-5}$ | <<1% | <1% |
| VIII | Example 29 | 506 | $4 \times 10^{-4}$ | 18.1% | 24.3% |

What is claimed is:

1. A compound of the formula I

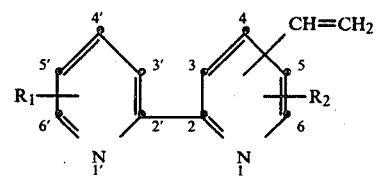

wherein the vinyl group is bonded in the 4-position or 6-position, $R_1$ is hydrogen, $C_{1-6}$-alkyl, $C_{1-6}$-alkoxy, phenyl or phenoxy and $R_2$ is hydrogen or methyl, with the proviso that one of $R_1$ and $R_2$ is not hydrogen, if the vinyl group is bonded in the 6-position.

2. A compound of the formula I according to claim 1, wherein the vinyl group is bonded in the 4-position, $R_1$ is hydrogen or $C_{1-4}$-alkyl bonded in the 4'-position, 5'-position or 6'-position and $R_2$ is hydrogen or methyl.

3. A compound of the formula I according to claim 1, wherein the vinyl group is bonded in the 4-position, $R_1$ is methyl bonded in the 4'-position or 6'-position and $R_2$ is hydrogen, or $R_1$ is hydrogen and $R_2$ is methyl bonded in the 6-position.

4. A compound of the formula XIII

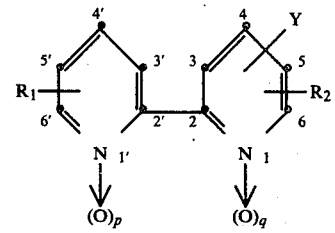

in which $R_1$ is hydrogen, $C_{1-6}$-alkyl, $C_{1-6}$-alkoxy, phenyl or phenoxy, $R_2$ is hydrogen or methyl, Y is methyl or —CH$_2$OCOR' bonded in the 4-position or 6-position and R' is $C_{1-5}$-alkyl, and p is zero or the number 1 and q is the number 1, if Y is methyl, or p is the number 1 and q is zero, if Y is —CH$_2$OCOR'.

5. A compound of the formula XIV

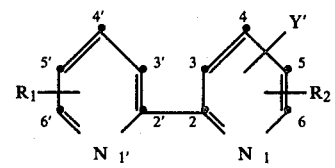

in which $R_1$ is hydrogen, $C_{1-6}$-alkyl, $C_{1-6}$-alkoxy, phenyl or phenoxy, $R_2$ is hydrogen or methyl, Y' is —CH$_2$O-COR' —CH$_2$OH, —CH$_2$Cl, —CH$_2$Br or —CH$_2$P+(R")$_3$, which are bonded in the 4-position or 6-position, or Y' is —CH$_2$CH$_2$OH or —CH$_2$CH$_2$OCH$_2$R, which are bonded in the 4-position, R is phenyl which is unsubstituted or substituted by $C_{1-6}$-alkyl or $C_{1-6}$-alkoxy, R' is $C_{1-5}$-alkyl and the R" independently of one another are $C_{1-5}$-alkyl or phenyl which is unsubstituted or is monosubstituted or disubstituted by $C_{1-4}$-alkyl or $C_{1-4}$-alkoxy.

6. A compound according to claim 1, of the formula

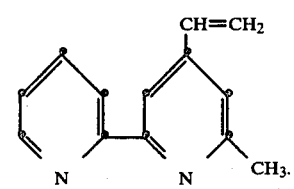

* * * * *